(12) United States Patent
Yang et al.

(10) Patent No.: US 7,728,839 B2
(45) Date of Patent: Jun. 1, 2010

(54) DISCRIMINATIVE MOTION MODELING FOR HUMAN MOTION TRACKING

(75) Inventors: Ming-Hsuan Yang, Sunnyvale, CA (US); Zhimin Fan, Beijing (CN)

(73) Assignee: Honda Motor Co., Ltd., Tokyo (JP)

( * ) Notice: Subject to any disclaimer, the term of this patent is extended or adjusted under 35 U.S.C. 154(b) by 24 days.

(21) Appl. No.: 11/553,374

(22) Filed: Oct. 26, 2006

(65) Prior Publication Data

US 2007/0103471 A1    May 10, 2007

Related U.S. Application Data

(60) Provisional application No. 60/731,158, filed on Oct. 28, 2005.

(51) Int. Cl.
*G06T 7/20* (2006.01)
(52) U.S. Cl. ...................................... 345/474
(58) Field of Classification Search ................... None
See application file for complete search history.

(56) References Cited

U.S. PATENT DOCUMENTS

| | | | | |
|---|---|---|---|---|
| 5,263,098 A * | 11/1993 | Horikami | ..................... | 382/128 |
| 5,353,132 A * | 10/1994 | Katsuma | ..................... | 358/539 |
| 5,943,435 A * | 8/1999 | Gaborski | ..................... | 382/132 |
| 6,295,367 B1 | 9/2001 | Crabtree et al. | | |
| 6,483,940 B1 * | 11/2002 | Wang | ..................... | 382/164 |
| 6,591,146 B1 * | 7/2003 | Pavlovic et al. | ............... | 700/29 |
| 6,778,705 B2 * | 8/2004 | Gutta et al. | ................. | 382/224 |
| 6,947,042 B2 * | 9/2005 | Brand | ........................ | 345/428 |
| 6,985,172 B1 * | 1/2006 | Rigney et al. | ............... | 348/149 |
| 7,092,566 B2 * | 8/2006 | Krumm | ..................... | 382/170 |

OTHER PUBLICATIONS

Belhumeur et al. Eigenfaces vs. Fisherfaces: Recognition Using Class Specific Linear Projection. IEEE Transactions on Pattern Analysis and Machine Intelligence. vol. 19. Issue 7. Jul. 1997.*

Yan et al. Discriminant Analysis on Embedded Manifold. European Conference on Computer Vision. 2004.*

Yang et al. Two-dimensional PCA: a new approach to appearance-based face representation and recognition. IEEE Transactions on Pattern Analysis and Machine Intelligence. vol. 26. Issue 1. Jan. 2004.*

Raja et al. Segmentation and Tracking Using Color Mixture Models. Proceedings of the Third Asian Conference on Computer Vision. vol. 1. 1998.*

(Continued)

*Primary Examiner*—Peter-Anthony Pappas
(74) *Attorney, Agent, or Firm*—Fenwick & West LLP; Mark Duell

(57) ABSTRACT

A system and method recognizes and tracks human motion from different motion classes. In a learning stage, a discriminative model is learned to project motion data from a high dimensional space to a low dimensional space while enforcing discriminance between motions of different motion classes in the low dimensional space. Additionally, low dimensional data may be clustered into motion segments and motion dynamics learned for each motion segment. In a tracking stage, a representation of human motion is received comprising at least one class of motion. The tracker recognizes and tracks the motion based on the learned discriminative model and the learned dynamics.

25 Claims, 7 Drawing Sheets

OTHER PUBLICATIONS

Dalal et al. Histograms of Oriented Gradients for Human Detection. IEEE Computer Society Conference on Computer Vision and Pattern Recognition. vol. 1. Jun. 2005.*

Urtasun et al. Priors for People Tracking from Small Training Sets. Proceedings of the Tenth IEEE International Conference on Computer Vision. Oct. 15-21, 2005.*

Morris et al. Singularity Analysis for Articulated Object Tracking. Proceedings of the IEEE Computer Society Conference on Computer Vision and Pattern Recognition. Jun. 23-25, 1998.*

Ju et al. Cardboard People: A Parameterized Model of Articulated Image Motion. Proceedings of the Second International Conference on Automatic Face and Gesture Recognition. Oct. 14-16, 1996.*

Brand et al. Style Machines. Proceedings of the 27th Annual Conference on Computer Graphics and Interactive Techniques. 2000.*

Mikolajczyk et al. A Performance Evaluation of Local Descriptors. IEEE Transactions on Pattern Analysis and Machine Intelligence. vol. 27. Issue 10. Oct. 2005.*

Agarwal et al. Tracking Articulated Motion using a Mixture of Autoregressive Models. European Conference on Computer Vision. May 2004.*

Mowbray et al. Automatic Gait Recognition via Fourier Descriptors of Deformable Objects. Audio Visual Biometric Person Authentication. 2003.*

Magee et al. Building Class Sensitive Models for Tracking Applications. Proceedings of the British Machine Vision Conference. 1999.*

Dhillon et al. Class Visualization of High-Dimensional Data with Applications. Computational Statistics & Data Analysis. vol. 41. Issue 1. 2002.*

Cao et al. Expressive Speech-Driven Facial Animation. ACM Transactions on Graphics. vol. 24. Issue 4. Oct. 2005.*

Yam et al. Gait Recognition by Walking and Running: A Model-Based Approach. Asian Conference on Computer Vision. Jan. 2002.*

Bowden. Learning Statistical Models of Human Motion. Computer Vision and Pattern Recognition. 2000.*

Tanco et al. Realistic Synthesis of Novel Human Movements from a Database of Motion Capture Examples. Proceedings of the Workshop on Human Motion. 2000.*

Agarwal, A., et al., "Tracking Articulated Motion Using a Mixture of Autoregressive Models," Proceedings of the $8^{th}$ European Conference on Computer Vision, 2004, 12 pages.

Chen, H., et al., "Local Discriminant Embedding and Its Variants," Proceedings of the IEEE Conference on Computer Vision and Pattern Recognition, 2000, pp. 126-133.

Felzenszwalb, P. F., et al., "Efficient Matching of Pictorial Structures," Proceedings of the IEEE Conference on Computer Vision and Pattern Recognition, 2000, pp. 66-73.

He, X., et al., "Locality Preserving Projections," Proceedings, Neural Information Processing Systems (NIPS), 2003, 8 pages.

Li, Y., et al., "Motion Texture: A Two-Level Statistical Model for Character Motion Synthesis," ACM Computer Graphics (SIGGRAPH), 2002, pp. 465-472.

North, B., et al., "Learning and Classification of Complex Dynamics," IEEE Transactions on Pattern Analysis and Machine Intelligence, Sep. 2000, pp. 1016-1034, vol. 22, No. 9.

Roweis, S. T., et al., "Nonlinear Dimensionality Reduction by Locally Linear Embedding," Science, Dec. 22, 2000, pp. 2323-2326, vol. 290.

Sminchisescu, C., et al., "Generative Modeling for Continuous Non-Linearly Embedded Visual Inference," Proceedings of the $21^{st}$ International Conference on Machine Learning (ICML), 2004, 8 pages.

Tenenbaum, J. B., et al., "A Global Geometric Framework for Nonlinear Dimensionality Reduction," Science, Dec. 22, 2000, pp. 2319-2323, vol. 290.

Wang, Q., "Learning Object Intrinsic Structure for Robust Visual Tracking," Proceedings of the 2003 IEEE Computer Society Conference on Computer Vision and Pattern Recognition (CVPR'03), 2003, pp. 227-233.

Yan, S., et al., "Graph Embedding: A General Framework for Dimensionality Reduction," Proceedings of the IEEE Conference on Computer Vision and Pattern Recognition, 2005, pp. 830-837.

Sminchisescu, C., et al., "Estimating Articulated Human Motion with Covariance Scaled Sampling," International Journal of Robotics Research, 2003, pp. 371-393, vol. 22, No. 6., [online] [retrieved on Nov. 27, 2006] Retrieved from the Internet: <URL: http://www.cs.toronto.edu/~crismin/PAPERS/css_ijrr03.pdf>.

Sminchisescu, C., et al. "Learning to Reconstruct 3D Human Motion from Bayesian Mixtures of Experts. A Probabilistic Discriminative Approach," Technical Report, University of Toronto, Oct. 2004, pp. 1-28, CSRG-502, [online] [retrieved on Nov. 27, 2006] Retrieved from the Internet: <URL: http://www.cs.toronto.edu/~crismin/PAPERS/csrg502.pdf>.

Zhao, T., et al., "3D Tracking of Human Locomotion: A Tracking as Recognition Approach," University of Southern California, Institute for Robotics and Intelligent Systems, pp. 1-6, Los Angeles, CA., [online] [retrieved on Nov. 27, 2006] Retrieved from the Internet: <URL: http://iris.usc.edu/Outlines/papers/2002/zhao-icpr02.pdf>.

PCT International Search Report and Written Opinion, PCT/US06/42088, Nov. 3, 2008, 14 Pages.

* cited by examiner

Tracking Stage
220

DISCRIMINATIVE MOTION MODELING FOR HUMAN MOTION TRACKING

RELATED APPLICATIONS

This application claims priority from U.S. provisional application No. 60/731,158 entitled "Discriminative Motion Modeling For Human Motion Tracking" which is incorporated by reference herein in its entirety.

FIELD OF THE INVENTION

The invention relates generally to computer vision, and more specifically, to tracking human motion.

BACKGROUND OF THE INVENTION

Many applications in computer vision involve motion analysis and modeling, such as motion tracking and action recognition. Most conventional methods for motion modeling are largely limited to simple motions. A comprehensive analytical model for complex motions, such as biological motion or human motion, is a challenging problem. One of the difficulties in motion modeling stems from the high dimensionality of the complex motion, which demands great descriptive power from the model itself. Without any constraint, it is very difficult, if not impossible, to model arbitrary motions. Fortunately, in practice, the motions of interest are more or less constrained due to physical or biological reasons. Although these constraints can be highly nonlinear, they largely reduce the intrinsic complexity of the motion. For example, human motions cannot be arbitrary but must be confined by anthropologically feasible joint angles, e.g., the upper arm and the lower arm cannot move independently.

Thus, one issue in motion tracking is to characterize and take advantage of these constraints. Since it is generally difficult to explicitly describe motion constraints, a plausible alternative is to learn them from training data. Human motion, although complex, resides in a space whose dimensionality is significantly lower than its joint angle space. Thus, dimensionality reduction is a significant step of learning to help reduce the problem complexity and build a motion model.

Many conventional techniques are available for dimensionality reduction in human motion tracking. One conventional technique is to reduce the dimensionality using ISO-MAPS and learn a Gaussian mixture model in the low-dimensional space as described in Tenenbaum, J. B., et al., *A Global Geometric Framework For Nonlinear Dimensionality Reduction,* Science, 2000, vol. 290 pp. 2319-2323 which is incorporated by reference herein in its entirety. Another conventional technique is to use Laplacian eigenmaps for dimensionality reduction, and employ continuity interpolation when modeling dynamics as described in Sminchisescu, C., and A. Jepson, *Generative Modeling for Continuous Non-Linearity Embedded Visual Inference,* ICML, 2004 which is incorporated by reference herein in its entirety. In yet another conventional technique, K-means clustering is used to partition the state space first, and then Principal Component Analysis (PCA) is used to reduce the dimensionality.

These conventional methods are suitable when the motion is short, uniform and continuous, but are inappropriate for recognizing and tracking different motion patterns. These techniques may introduce confusion among different motion classes due to the compactness in the low-dimensional space and prevent accurate tracking.

There have been several previous attempts to deal with training data comprising multiple classes of motion. For example, a transition probability matrix may be learned as described in Wang, Q., et al., *Learning Object Intrinsic Structure for Robust Visual Tracking,* Proc. IEEE Conference on Computer Vision and Pattern Recognition, 2003, pp. 227-233 and North, B., et al.,*Learning and Classification of Complex Dynamics,*IEEE Transactions on Pattern Analysis and Machine Intelligence, 2000, pp. 1016-1034 which are both incorporated by reference herein in their entirety. An alternative to the transition matrix is to apply the training algorithm repeatedly for each individual motion. A problem that confronts these two methods is that it is possible that the different motions to be tracked may have some similar human poses, and these poses may be even closer when the dimensionality of the data is reduced. When the tracker is approaching these confusion areas caused by these similar poses, the tracker can be distracted since there is no discriminance enforced among those possible motion patterns. When motion segments with different characteristics are intermingled together, the accuracy of motion modeling may deteriorate.

Due to the problems above, the preservation of differences between motion patterns in the training set is a significant property when tracking multiple classes of motion. Therefore, it is also preferable to maintain the discriminance between motions in the lower dimensional space. Traditional discriminative models such as Linear Discriminative Analysis (LDA) are inappropriate for this problem because the motions to be modeled are generally non-linear and non-Gaussian.

What is needed as a system for discriminative motion modeling that can recognize and track a variety of human motion patterns in a reduced dimensionality space.

SUMMARY OF THE INVENTION

A system and method is provided to efficiently recognize and track a set of stylized human motions. A representation of human motion is received having at least one motion from a motion class. A motion comprises a sequence of pose states residing in a high dimensional space. A discriminative model is received, for example, from an offline learning stage to project the sequences of pose states from the high dimensional space to a low dimensional space. The discriminative model enforces discriminance between the different classes of motion in the low dimensional space. The tracker can accurately and efficiently track motions from different motion classes based on the learned discriminative model. This framework is general and does not require restrictions on the selection of the stylized motions to be tracked.

In one embodiment, in order to preserve the discriminance in the low-dimensional space, the discriminative model projects data points that are near neighbors in the original space so that they are still the near neighbors in the low-dimensional space. Also, the neighbor data points in the original space from different motion classes are separated as far as possible in the low-dimensional space.

In on embodiment of the learning stage, the model of the human body is represented as a skeleton and body parts. A pose state vector represents the pose of the skeleton and each motion type is represented by a sequence of such vectors. Vectors in the high dimensional space are projected onto a low-dimensional space by a dimensionality reduction algorithm. A clustering algorithm is applied to the low-dimensional data to generate a set of motion segments, and an autoregressive process (ARP) is learned for each motion segment.

In one embodiment of the tracking stage, the initialized skeleton is projected onto the low-dimensional space. The nearest neighbor(s) of the current skeleton is then computed, and the corresponding possible motion type(s) of these neighbors are determined. The discriminative motion model helps the tracker to be selective with these nearest neighbors, especially when multiple motion classes are tracked. The learned dynamics are then used to predict the future skeleton pose in the low-dimensional space and can be reconstructed to the original space. Finally, the body parts hypotheses and the predicted skeleton determine the tracking result interactively.

DETAILED DESCRIPTION OF THE INVENTION

Figure 1:
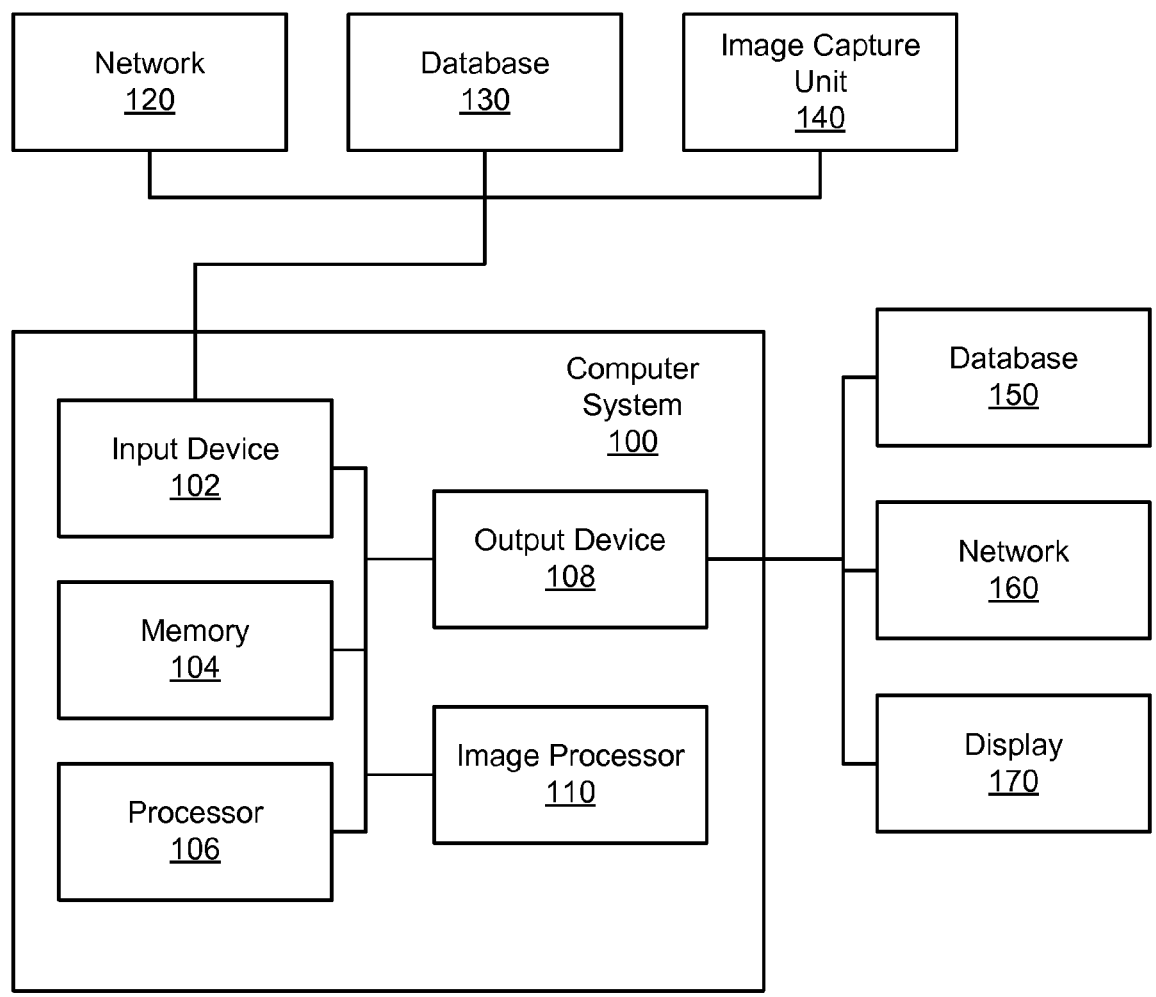
FIG. 1 is a computer system in accordance with one embodiment of the present invention.

A preferred embodiment of the present invention is now described with reference to the figures where like reference numbers indicate identical or functionally similar elements. Also in the figures, the left most digit of each reference number corresponds to the figure in which the reference number is first used.

Reference in the specification to "one embodiment" or to "an embodiment" means that a particular feature, structure, or characteristic described in connection with the embodiments is included in at least one embodiment of the invention. The appearances of the phrase "in one embodiment" in various places in the specification are not necessarily all referring to the same embodiment.

Some portions of the detailed description that follows are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "determining" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

In addition, the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the claims.

FIG. 1 is a computer system according to one embodiment of the present invention. The computer system 100 comprises an input device 102, a memory 104, a processor 106, an output device 108, and an image processor 110. The input device 102 is coupled to a network 120, a database 130, and an image capture unit 140. The output device 108 is coupled to a database 150, a network 160, and a display 170. In other embodiments, the input device is connected to only one or two of a network 120, a database 130, and an image capture unit 140. In yet another embodiment, the input device may be connected to any device configured to input data to the computer system. Similarly, in some embodiments, the output device may be connected to one or more of a database 150, network 160, display 170 or any other device cable of receiving outputted data. In another embodiment, the computer system comprises one or more of a processor 106, an image processor 110, or other specialized processor.

Figure 2:
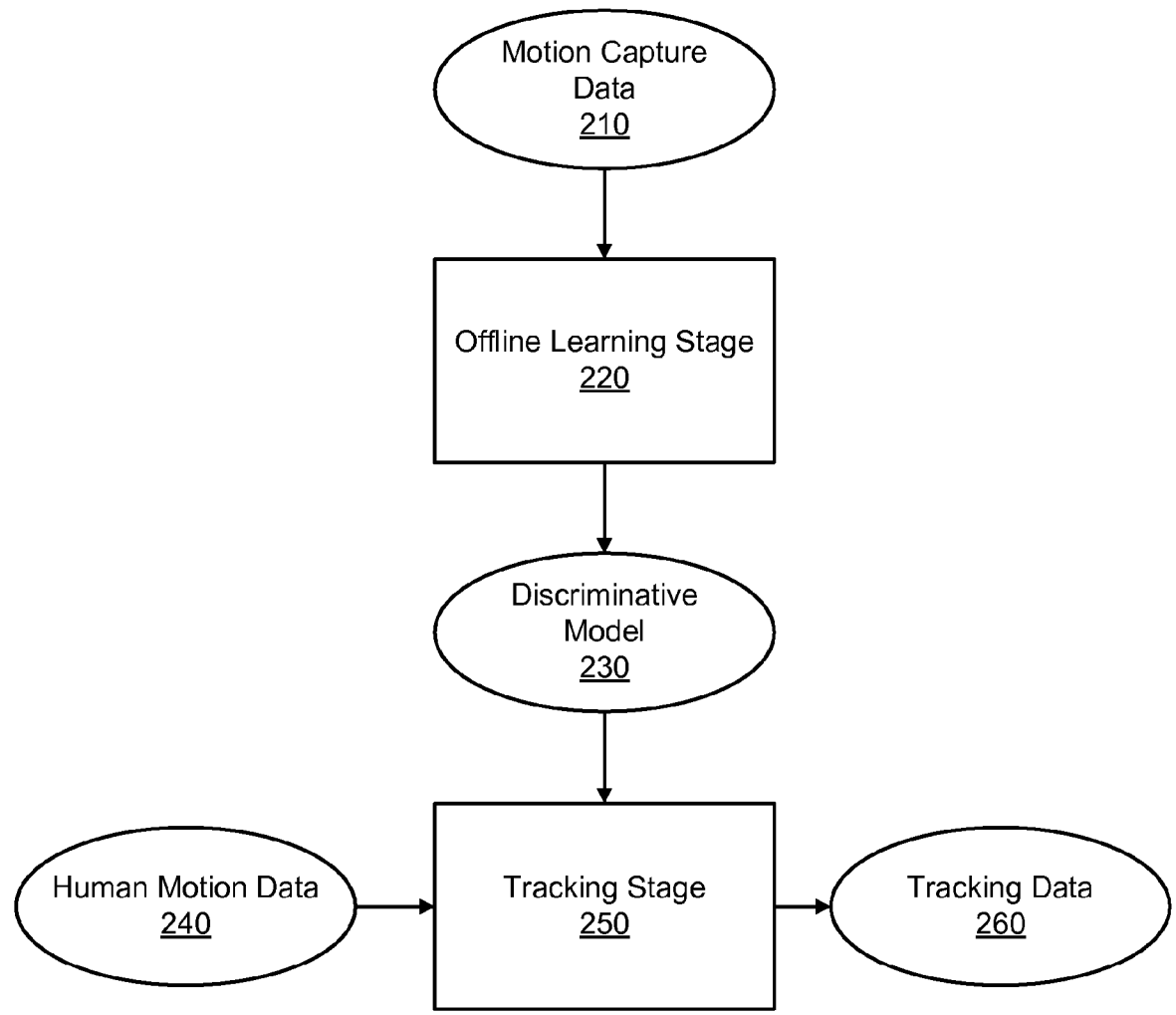
FIG. 2 is an input/output diagram in accordance with one embodiment of the present invention.

FIG. 2 is an input/output diagram according to one embodiment of the present invention. In an offline learning stage 220 a discriminative model 230 is generated based on motion capture data 210. A tracking stage 250 receives the discriminative model 230 and human motion data 240 (such as a video) comprising at least one motion to be tracked. Based on the learned discriminative model 230, the tracking stage outputs tracking data 260.

The motion capture data 210 comprises data of at least one motion class. For example, a motion class may be walking, clapping, tossing, balancing, or swinging. Motion capture data 210 may be acquired by a variety of conventional techniques. In one embodiment, a subject wears a special suit with markers and performs motions captured by a video camera or similar device. Further, motion capture data 210 may be two dimensional or three dimensional. Motion capture data 210 may be acquired from multiple subjects performing the same classes of motions. This provides the statistical data used to generate the deterministic model 230.

In the learning stage, motion capture data 210 is received 302 by the computer system 100. In one embodiment, the motion capture data 210 may be received by a image capture unit 140 interfaced to an input device 102. In other embodiments, the motion capture data 210 may be received by the input device 102 from a database 130 or through a network 120.

Figure 4:
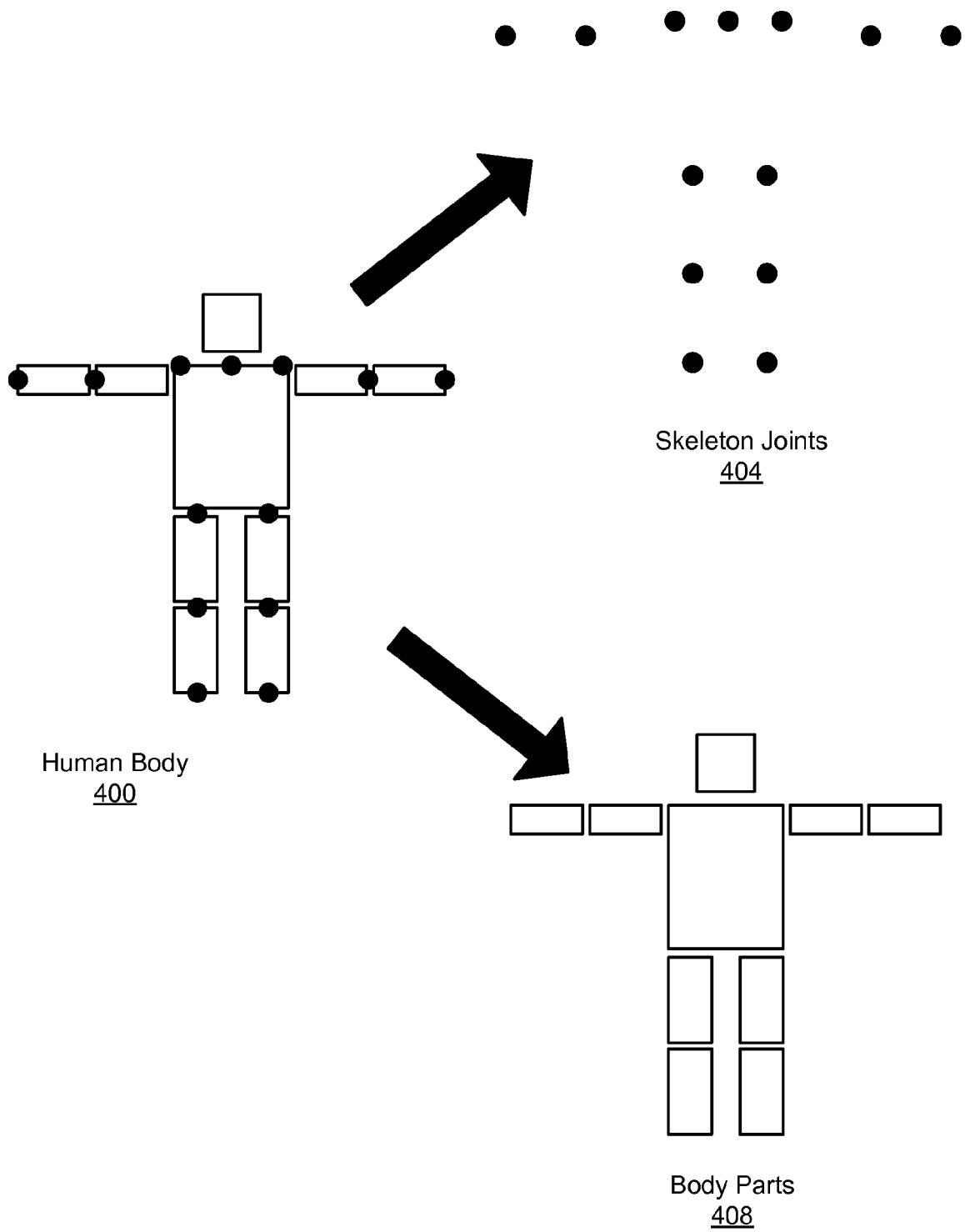
FIG. 4 is a human body model in accordance with one embodiment of the present invention.

Motion capture data is processed 304 to extract pose states. Processing may be performed by a processor 106, image processor 110, or other specialized processor. An example of the pose state representation is illustrated in FIG. 4. In this example embodiment, a human body 400 includes a pose state comprising skeleton joints 404. The pose state is represented by a vector, x. For example, x may represent the relative coordinates of skeleton joints 404. In another embodiment, the pose state vector, x, may instead represent other characteristics that describe the pose state. For example, the pose state vector, x, may represent angles, positions, velocities, or accelerations of joints, limbs, or other body parts or points of interest used to describe the pose state. A motion is composed of a time sequence of pose states, and is represented by a sequence of vectors $X=[x_1 \, x_2 \ldots x_m]$. Each pose state vector, $x_i$, may be assigned a motion label $y_i$. The motion label $y_i$ represents the class of motion to which the pose state vector, $x_i$, belongs.

The sequence of vectors, X, representing a motion resides in a high dimensional space, denoted by $H \in R^n$ where R is the space of real numbers and n is the dimensionality of the high dimensional space. For example, if 13 skeleton joints 404 are used to represent the pose (as in FIG. 4), each pose state vector, x, would have n=26 dimensions, representing the concatenated two dimensional image coordinates of the 13 skeleton joints 404. In another embodiment, the pose state vector, x, may comprise three dimensional image coordinates. Processing data in this high dimensional space is computationally expensive and inefficient, making real-time tracking difficult or impossible. Therefore, it is desirable to project the high-dimensional data to a low-dimensional space denoted by $L \in R^l$ where l is the dimensionality of the low dimensional space. This projection becomes possible given that human motion is naturally constrained due to physical or biological reasons. For example, the upper arm and lower arm cannot move independently and there are a limited number of anthropologically feasible joint angles.

Figure 3:
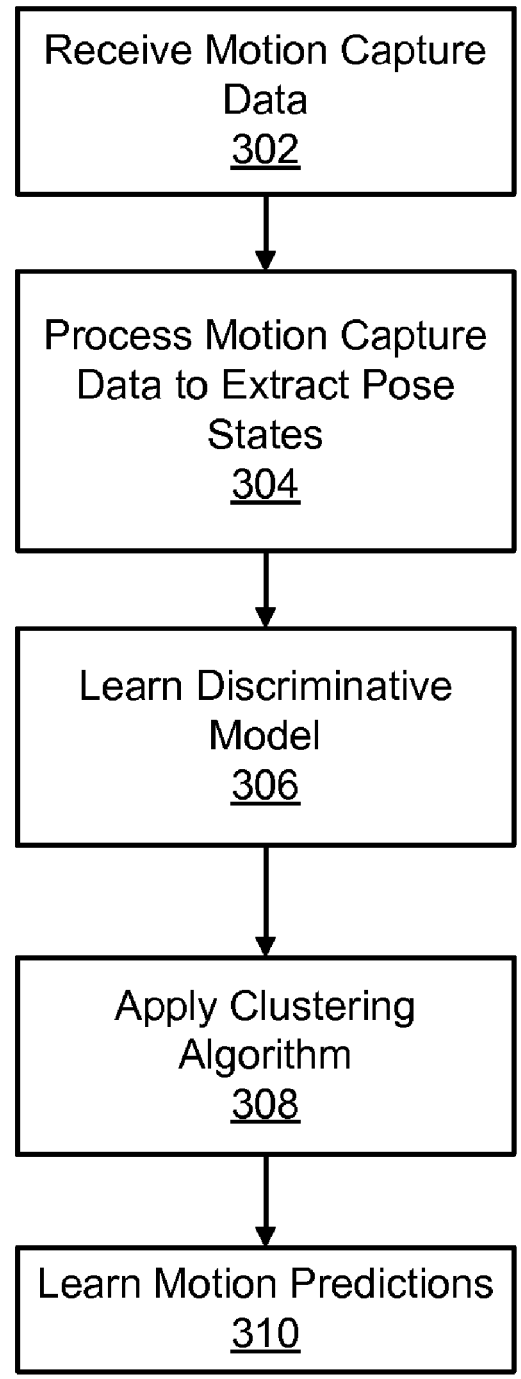
FIG. 3 is a flow diagram illustrating an offline learning stage in accordance with one embodiment of the present invention.

Turning back to FIG. 3, a discriminative model is learned 306 to project the high-dimensional data, X, to a low dimensional space. The discriminative model obtains low-dimensional state vectors $Z=[z_1 \, z_2 \ldots z_m]$, where the dimensionality, l, of each $z_i$ is less than the dimensionality, n, of each $x_i$. In reducing the dimensionality of the data, the discriminative model also enforces discriminance between different classes of motion. By enforcing discriminance, the model projects data such that samples which are near neighbors in the high dimensional space and of the same motion class remain near neighbors in the low-dimensional space. Samples which are near neighbors but from different motion classes are separated as far as possible in the low-dimensional space.

For example, a pose state vector $x_a$ of the motion class "clap" may appear very similar to a pose state vector $x_b$ of the motion class, "swing". The discriminative model will project the data such that the low dimensional state vectors $z_a$ and $z_b$ are far apart in the low dimensional space. In contrast, if a pose state vectors $x_a$ and $x_c$ are both of the motion class "clap" and appear very similar in the high dimensional space, the discriminative model will project the data such that $z_a$ and $z_c$ remain similar in the low dimensional space. The discriminative model is thus configured to avoid confusion areas between different classes of motions and allows for accurate tracking of multiple motion classes.

The discriminance between the data from different motion classes is achieved by increasing the inter-class separability, which is the sum of the distances between each data point and their neighboring data points that are from different classes, and simultaneously reducing the intra-class variety, which is the sum of the distances between each point and their neighboring points that are in the same class. The advantage of contriving these two measurements is that in contrast to many conventional techniques, it does not rely on the assumption that the data follows Gaussian distribution.

In one embodiment, Local Discriminant Embedding (LDE) (or similar Marginal Fisher Analysis) provides the discriminative model 230 to project data from the high dimensional space to the low dimensional space. LDE and Marginal Fisher Analysis are described in more detail in Chen, H., et al., *Local Discriminant Embedding and Its Variants*, Proc. IEEE Conference on Computer Vision and Pattern Recognition, 2000, pp. 126-133; and Yan, et al., *Graph Embedding: A General Framework for Dimensionality Reduction*, Proc. IEEE Conference on Computer Vision and Pattern Recognition, 2005, pp. 830-837, which are both incorporated by reference herein in their entirety. Additional details may be found in He, X., *Locality Preserving Projections*, NIPS, 2003 which is incorporated by reference herein in its entirety.

Figure 5:
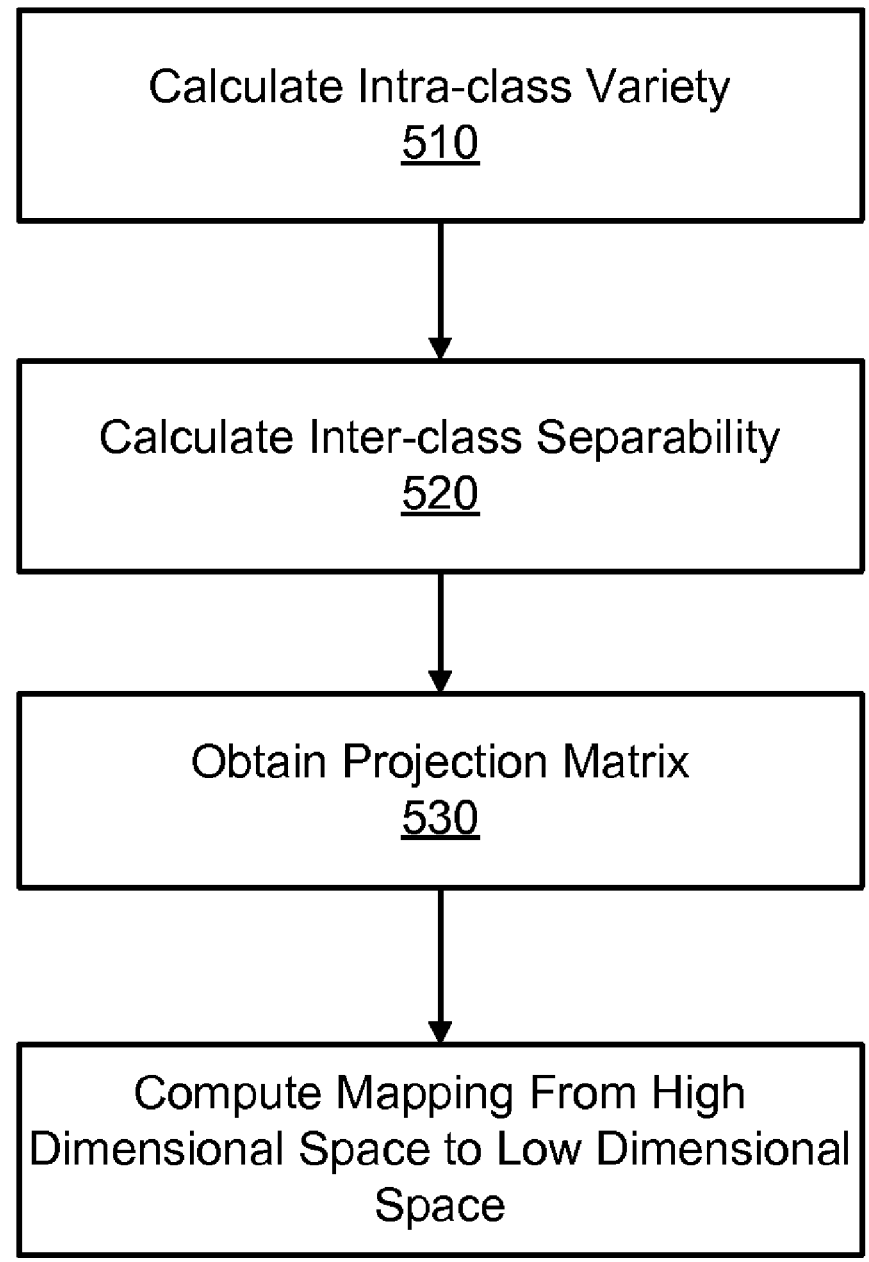
FIG. 5 is a flow diagram illustrating a method for applying a discriminative model in accordance with one embodiment of the present invention.
Figure 6:
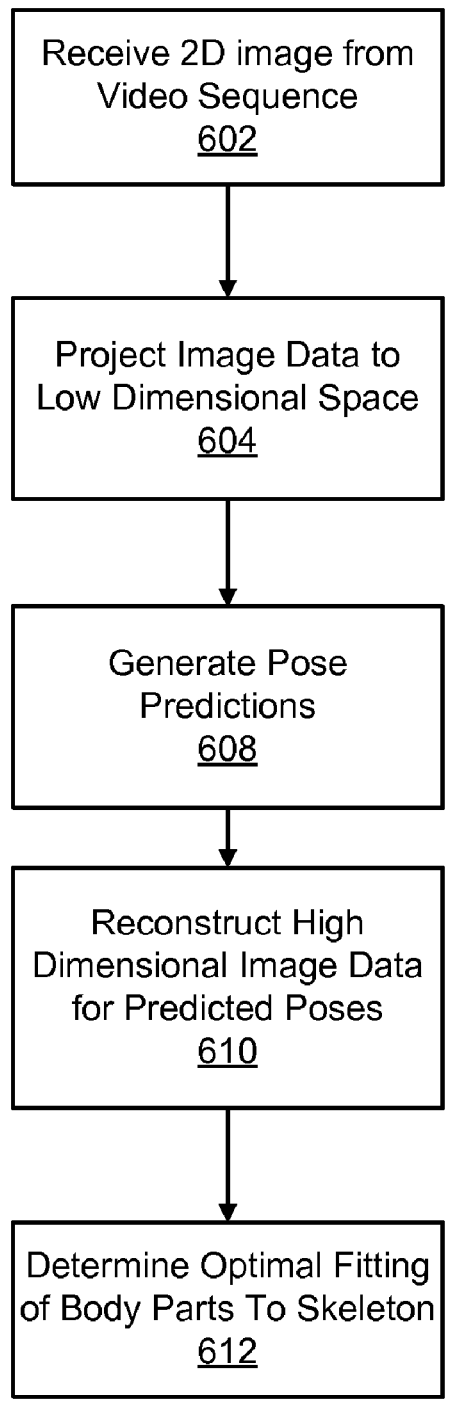
FIG. 6 is a flow diagram illustrating a tracking stage in accordance with one embodiment of the present invention.

FIG. 5 illustrates one embodiment of a method for learning 306 the discriminative model. For the motion data set $X=[x_1 \, x_2 \ldots x_m] \in H$, a projection matrix V generates the low dimensional data by $Z=V^T X=[z_1 \, z_2 \ldots z_m] \in L$. The class label for each $x_i$ is $y_i$.

The intra-class variety is computed 510 as $$^{i,j} i\in N_{k_1}^+(j) \text{ or } j\in N_{k_1}^+(i)$$

$$S_w = \sum_{i,j} \sum_{i\in N_{k_1}^+(j) \text{ or } j\in N_{k_1}^+(i)} \|W_{x_i} - W_{x_j}\|^2 \quad (1)$$

$$= 2W^T X (D^w - W^w) X^T W$$

$$W_{ij}^w = 1 \text{ if } j \in N_{k_1}^+(i) \text{ or } i \in N_{k_1}^+(j); 0, \text{ else}$$

where $N_{k_1}^+(i)$ denotes the set of $k_1$ nearest neighbors of point $x_i$, which are in the same class of class $y_i$. $D^w$ is a diagonal matrix with entries $d_{ii}^w = \Sigma_j W_{ij}^w$ The inter-class separability is computed 520 as $$^{i,j} i\in N_{k_2}^-(j) \text{ or } j\in N_{k_2}^-(i)$$

$$S_b = \sum_{i,j} \sum_{i\in N_{k_2}^-(j) \text{ or } j\in N_{k_2}^-(i)} \|W_{x_i} - W_{x_j}\|^2 \quad (2)$$

$$= 2W^T X (D^b - W^b) X^T W$$

$$W_{i,j}^b = 1 \text{ if } j \in N_{k_2}^-(i) \text{ or } i \in N_{k_2}^-(j); 0, \text{ else}$$

where $N_{k_2}^-(i)$ denotes the set of $k_2$ nearest neighbors of point $x_i$, which are in classes other than $y_i$. $D^b$ is a diagonal matrix with entries $d_{ii}^b = \Sigma_j W_{ij}^b$ Then, the projection matrix, V, can be obtained 530 by solving the following generalized eigenvector problem, $$X(D^b - W^b)X^T v = \lambda X(D^w - W^w)X^T v \quad (3)$$

Eigenvectors $v_1, v_2, \ldots, v_l$ are chosen corresponding to the l largest eigenvalues. The mapping from the high dimensional space to the low dimensional space can then be computed 540 by $z_i = V^T x_i$, where $V = [V_1, V_2, \ldots, V_l]$.

A dynamic human motion model can further improve motion tracking. Motion can be practically modeled as an autoregressive process by recognizing that the movement in a short period tends to be continuous. This model is based in part on techniques described in Wang and North referenced previously; and Agarwal, A. and B. Triggs, *Tracking Articulated Motion Using a Mixture of Autoregressive Models*, ECCV, 2004; and Li, Y., et al., *Motion Texture: A Two-Level Statistical Model for Character Motion Synthesis*, SIGGRAPH, 2002 which are both incorporated by reference herein in their entirety.

A clustering algorithm is applied 308 to separate the data of each motion pattern in the low dimensional space into clusters. In one embodiment, a K-means algorithm provides the clustering algorithm. To ensure that each cluster is formed by contiguous sequences, the time stamp $t_i$ of each sample point $z_i$ is also considered. Thus, in one embodiment, similar low dimensional state vectors, z, that have very different time stamps, t, are clustered separately. For example, if low dimensional state vectors $z_a$ and $z_b$ are very similar and are very close together in time, it is highly likely the state vectors are part of the same motion segment and should be clustered together. However, if the similar state vectors are far apart in time, it is less likely they are part of the same motion segment and may instead represent similar poses from different motion segments. Thus, the clustering algorithm encourages temporally contiguous sample vectors to be clustered into one segment.

Motion dynamics are learned 310 for each motion segment to help guide the tracking. Motion dynamics may comprise two-dimensional or three dimensional motions. In one embodiment, an auto-regressive process (ARP) is applied to learn the motion patterns of each segment by $$z_t = \sum_{k=1}^{K} A_k z_{t-k} + d + Bn, \quad (4)$$

where $z_t \in R^l$ is the state vector in the low-dimensional space, $A_k \in R^{l\times l}$; $k=1, \ldots, K$ is the state transition matrices for K clusters, d is the offset vector, $B \in R^{l\times l}$, $u_t \sim N(0, Q)$ is the noise vector. The parameters $\{A_k, k=1, \ldots, K, d, B\}$ can be learned by Maximum Likelihood Estimation (MLE) as described in North, et al., referenced above. Those motion segments, whose resulting prediction error by ARP is large, are considered to be erratic movements and are pruned away. The number of clusters in the clustering algorithm, K, is chosen as the one from a range, (for example, [1, 6]) which can produce the minimum ARP prediction error of all clusters.

The tracking stage 250 is configured to track a set of stylized motion patterns based on the learned model. In tracking, the human body can be represented by a human body model, for example, as illustrated in FIG. 4. In one embodiment, the data comprising the human body model is a combination of two subsets of parameters: pose state (represented by, for example, skeleton joints 402) and body parts 404. This decomposable model helps to distribute the computation into two subsets, each with reduced dimensionality. These two subsets jointly and interactively determine the human configuration, i.e., the skeleton joints 402 represents the abstract "style" of motions, which accounts for the general and global movement of human. The body parts 404 are the "content" of the motion, which are different for different people wearing different clothes.

The body parts 404 are represented by a set of body part descriptors. In one embodiment, rectangles associated with limbs, torso, and head, for example, represent each body part. In another embodiment, different shapes are used to represent the body parts. Each body part 404 has the parameters of center point, height, width, scale and orientation. The body parts 404 may then be manipulated with operations such as translation, rotation, scaling, and so on.

In one embodiment, various types of histograms are used as the body part descriptors. For example a color histogram, a gradient orientation histogram, and a color distance histogram may be used. A color histogram is a conventional histogram that represents an image by counts of the colors of each pixel in the image. A gradient orientation histogram is a representation that provides edge information in an image. Both the orientation and the magnitude of the gradient are computed for each pixel within the body part. Then the orientations are quantized into a predetermined number of bins and the magnitude of each gradient is added into its corresponding bin.

A color distance histogram represents the spatial distribution of color pixels. The color distance histogram describes how the color pixels are distributed within the body part, which can alleviate confusion between candidates which have similar color histogram but very different spatial distribution of color pixels. In computing the color distance histogram, the intensity range of the pixels is quantized into a predetermined number of bins. For each pixel, the pixel distance to the center of the body part is computed and the distance is added to the bin corresponding to the intensity of that pixel. Thus, both the intensity and the spatial structure of the color pixels are considered.

Figure 7:
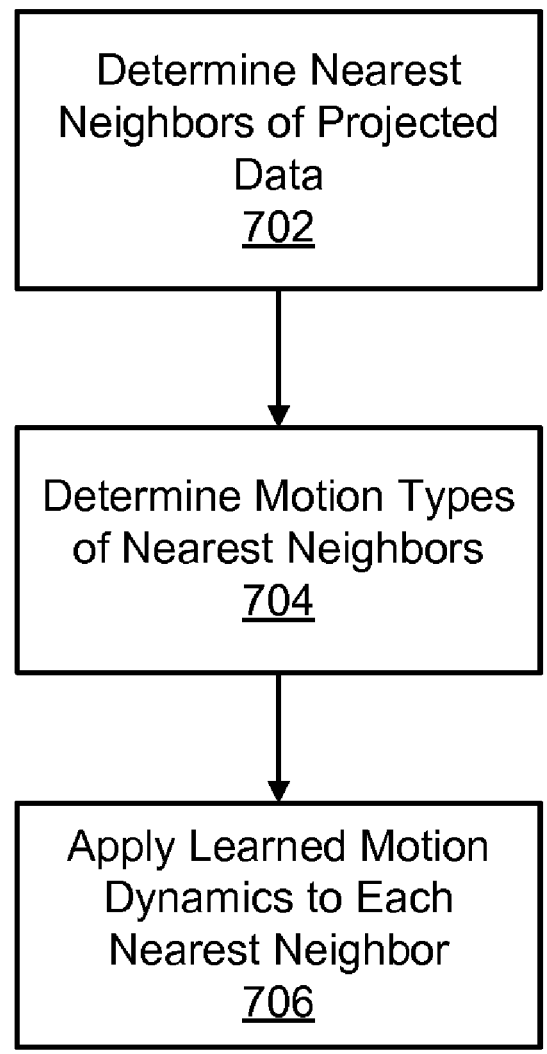
FIG. 7 is a flow diagram illustrating a method for generating pose predictions in accordance with one embodiment of the present invention.

In the tracking stage, 250, an image is received from the human motion data 240 (for example, a video) comprising the motion to be tracked. In one embodiment, no background subtracting is performed on the received image in contrast to many conventional techniques. The current skeleton vector, $x_c$, is projected 604 to the low dimensional space by $z_c = V^T x_c$ where V is the projection matrix generated in the learning stage 220. Pose predictions are then generated 608 to predict a future pose state of the skeleton. FIG. 7 illustrates one embodiment of a method for generating 608 pose predictions. The P nearest neighbors of $z_c$ are determined 702 where each of the P nearest neighbors come from different motion segments. In one embodiment, P is a predetermined quantity. The motion type of each of the P nearest neighbors are then determined 704. The learned motion dynamics of the P different motion segments are applied 706 to form the pose predictions for each nearest neighbor. Thus, predictions are generated 608 based on learned motion dynamics for different motion segments. In one embodiment, pose predictions are generated using the auto-regressive process of Eq. 4 described previously.

Given the skeleton configuration in the low-dimensional space, L, the corresponding skeleton is reconstructed 610 in the original space, H for the predicted poses. Here, the basic assumption is that, the local geometry is consistent in both the original space and the low-dimensional space. Neighborhood reconstruction is applied to reconstruct a predicted pose, $x_p$, in the original space from the predicted pose, $z_p$, in the low dimensional space in a manner similar to that described in Roweis, S. and L. K. Saul, *Nonlinear Dimensionality Reduction By Locally Linear Embedding*, Science, 2000, vol. 290, pp. 2323-2326 which is incorporated be reference herein in its entirety.

In reconstructing $x_p$ from $z_p$, the nearest neighbors of $z_p$ are first determined. Next, the linear coefficients that best reconstruct $z_p$ from the selected neighborhood are computed by a least square method. The neighborhood of $z_p$ in L has known corresponding states in H. $x_p$ is then reconstructed by linearly combining these states with the calculated coefficients.

In order to determine the optimal or near optimal combination of the body parts and the predicted skeleton, the body parts 404 must be fitted to the skeleton 402. Each of the body parts are fitted onto each of the possible predicted skeletons $S_p$, for $p=1, \ldots, P$. One way to represent the topology of the body parts is by a graph $G=(V, E)$, where the vertices $V=\{v_1, \ldots, v_Q\}$ correspond to the Q body parts (in FIG. 4, for example, Q=10). An edge $e(v_i, v_j)$ is assigned to each connected parts $v_i$ and $v_j$ such as the head and the torso, for example. The optimal fitting can be formulated as minimizing a cost function over the graph G, the parameters of which include the configuration of the skeleton $S_p$ and the configurations of all the Q body parts $B_i$, $i=1, \ldots, Q$.

For each body part $B_i$, the associated cost function $m(Bi)$ can be written as follows, $$m(B_i) = q(B_i, I) + d(B_i, S_p) \quad (5)$$

where, $q(B_i, I)$ measures how well the body part matches the image I when positioned as $B_i$, and $d(B_i, S_p)$ measures the extent to which the body part $B_i$ deviates from the skeleton $S_p$. There is also a cost over each edge $e(v_i, v_j) \in E$, which is the distance between those adjacent body parts, i.e., $d(B_i, B_j)$. The optimal solution is computed by $H^* = \{S^*, B_i^*, i=1, \ldots, Q\}$, such that $$H^* = \underset{B}{\arg\min} \left( \sum_{e(v_i, v_j) \in E} d(B_i, B_j) + \sum_{v_i \in V} m(B_i) \right) \quad (6)$$

Conventionally, solving the above optimization problem $\{S^*, B_i^*, i=1, \ldots, Q\}$ needs $O(Q^n F)$ time, where Q is the number of the body parts, n is the possible configurations of each body part, and F is the number of all possible skeletons. If there are no constraints on the configurations of the skeleton then $F=13^f$, where 13 is the number of the skeleton points, f is the number of possible locations of each skeleton point. Solving these equations these equations using conventional techniques brings overwhelming computational cost.

In contrast to conventional methods, computation is significantly reduced by restricting the number of the possible skeletons to only P predictions based on nearest neighbors as described previously. The discriminative motion modeling is well adapted to make this local neighborhood search because the model reduces confusion areas caused by the multiple motion classes in the training data. Computation may be further reduced by employing dynamic programming to make the body part fitting polynomial rather than exponential in time. This technique is based in part on the techniques used in Felzenszwalb, P. F., *Efficient Matching of Pictorial Structures*, Proc. IEEE Conference on Computer Vision and Pattern Recognition, 2000, pp. 66-73 which is incorporated by reference herein in its entirety.

For any vertex $v_j$ with no children (i.e., any leaf of the tree), its best configuration can be computed as a function of its parent $v_i$, $$B_j^*(B_i) = \arg \underset{B_j}{\min}(d(B_i, B_j) + m(B_j)) \quad (7)$$

For any vertex $v_j$ that has both parent $v_i$ and children, the best location of all its children can be known given the configuration of $B_j$. Let $C_{B_j}$ denote the best cost of all its children. Then the best configuration of $v_j$ is, $$B_j^*(B_i) = \arg \underset{B_j}{\min}(d(B_i, B_j) + m(B_j) + C_{B_j}) \quad (8)$$

For the root vertex $v_r$, its best configuration is found as, $$B_r^* = \arg \underset{B_r}{\min}(m(B_r) + C_{B_r}) \quad (9)$$

That is, fitting from the leaf parts can start, such as the lower arms and legs, then connects to their parents, i.e., the upper arms and legs, and finally reach to the root part, i.e., the head. Each non-leaf node records its best children given its own configuration. After that, the best configurations of each body part can be determined by tracing down from the root part to the leaf parts. The computation here is polynomial, $O(Qn^2)$.

While particular embodiments and applications of the present invention have been illustrated and described herein, it is to be understood that the invention is not limited to the precise construction and components disclosed herein and that various modifications, changes, and variations may be made in the arrangement, operation, and details of the methods and apparatuses of the present invention without departing from the spirit and scope of the invention as it is defined in the appended claims.

What is claimed is:

1. A method for recognizing and tracking human motion comprising steps of:
receiving, by an input device, a plurality of learned motion segments representing different learned motions within a motion class, wherein each learned motion segment comprises a plurality of state vectors and each state vector comprises a time stamp, and wherein one of the learned motion segments comprises temporally contiguous state vectors clustered together in a low-dimensional space based on the time stamps;
receiving, by the input device, a representation of human motion having at least one motion from the motion class, the at least one motion comprising a sequence of pose states represented in a high dimensional space;
processing the received representation according to computer-executable instructions stored in a memory that cause a processor to execute steps of:
projecting the sequences of pose states from the high dimensional space to the low dimensional space according to a discriminative model that when applied to the sequence of pose states increases the inter-class separability between pose states of different motion classes and decreases the intra-class separability between pose states of a same motion-class;
determining an integer P nearest neighbors of a first projected pose state in the low dimensional space, the P nearest neighbors from P different learned motion segments;
determining P pose predictions for the P different learned motion segments; and
determining the pose prediction that best matches a current frame of the representation of human motion; and
storing the determined pose prediction to a memory.

2. The method of claim 1 wherein determining the pose prediction that best matches a current frame of the representation of human motion comprises steps of:
reconstructing at least one pose prediction in the high dimensional space based on the discriminative model; and
determining an optimal matching of the at least one pose prediction in the high dimensional space to a current frame of the representation of human motion.

3. The method of claim 2 wherein determining an optimal matching comprises steps of:
representing the current frame by a human body model comprising coordinates of joints and body parts having shapes associated with limbs, torso and head;
representing each pose prediction in the high dimensional space by the human body model; and
selecting the pose prediction that optimally matches to the current frame based on the human body model.

4. The method of claim 3 wherein the human body model comprises body part descriptors including one or more of a color histogram, a gradient orientation histogram, and a color distance histogram.

5. The method of claim 1 wherein determining the P pose predictions comprises steps of:
determining a motion type of each of the nearest neighbors; and
applying a dynamic model to each of the nearest neighbors based on the motion type, the dynamic model learned in a learning stage.

6. The method of claim 1 wherein the discriminative model is received from a learning stage and wherein the learning stage is prior to said receiving steps, the learning stage comprising steps of:
receiving motion capture data from a motion capture source, the motion capture data comprising a first motion from a first motion class and a second motion from a second motion class that is different from the first motion class;
processing the motion capture data to extract a first sequence of pose states representing the first motion and a second sequence of pose states representing the second motion;
learning the discriminative model configured to project the first and second sequence of pose states to a low dimensional space and enforce discriminance between the first and second motion classes in the low dimensional space;
applying a clustering algorithm to cluster the temporally contiguous state vectors into the learned motion segments in the low dimensional space; and
learning a dynamic model for each motion segment to generate motion predictions in the low dimensional space.

7. The method of claim 6 wherein the clustering algorithm includes a k-means clustering algorithm.

8. The method of claim 6 wherein learning the discriminative model includes applying a Local Discriminant Embedding (LDE) model.

9. The method of claim 6 wherein learning a discriminative model comprises steps of:
computing an intra-class variety representing the sum of the distances between data points that are in the same motion class;
computing the inter-class separability representing the sum of the distances between data points that are in different motion classes;
obtaining a projection matrix configured to reduce the intra-class variety and increase the inter-class separability; and
projecting the motion capture data from the high dimensional space to the low dimensional space based on the projection matrix.

10. The method of claim 1 wherein the pose state comprises a vector of skeleton joint coordinates.

11. The method of claim 1 wherein the at least one motion is tracked without background subtraction.

12. The method of claim 1 wherein tracking the at least one motion comprises tracking the at least one motion in three dimensions.

13. A system for recognizing and tracking human motion comprising:
an input device for receiving a representation of human motion having at least one motion from a motion class, the at least one motion comprising a sequence of pose states represented in a high dimensional space, and for receiving a plurality of learned motion segments representing different learned motions within the motion class, wherein each learned motion segment comprises a plurality of state vectors and each state vector comprises a time stamp, and wherein one of the learned motion segments comprises temporally contiguous state vectors clustered together in a low-dimensional space based on the time stamps;
a processor adapted to project the sequences of pose states from the high dimensional space to the low dimensional space according to a discriminative model that when applied to the sequence of pose states, increases the inter-class separability between pose states of different motion classes and decreases the intra-class separability between pose states of a same motion class, determining an integer P nearest neighbors of a first projected pose state in the low dimensional space, the P nearest neighbors from P different learned motion segments, determining P pose predictions for the P different learned motion segments, and determining the pose prediction that best matches a current frame of the representation of human motion; and a memory adapted to store the determined pose state.

14. A computer program product, comprising a computer readable medium storing computer executable code for recognizing and tracking human motion, the computer executable code when executed causing a processor to perform steps of:

receiving a plurality of learned motion segments representing different learned motions within a motion class, wherein each learned motion segment comprises a plurality of state vectors and each state vector comprises a time stamp, and wherein one of the learned motion segments comprises temporally contiguous state vectors clustered together in a low-dimensional space based on the time stamps;

receiving a representation of human motion having at least one motion from the motion class, the at least one motion comprising a sequence of pose states represented in a high dimensional space;

projecting the sequences of pose states from the high dimensional space to the low dimensional space according to a discriminative model that when applied to the sequence of pose states increases the inter-class separability between pose states of different motion classes and decreases the intra-class separability between pose states of a same motion-class;

determining an integer P nearest neighbors of a first projected pose state in the low dimensional space, the P nearest neighbors from P different learned motion segments;

determining P pose predictions for the P different learned motion segments; and determining the pose prediction that best matches a current frame of the representation of human motion; and storing the determined pose prediction to a memory.

15. The computer program product of claim 14 wherein determining the pose prediction that best matches a current frame of the representation of human motion comprises steps of:

reconstructing at least one pose prediction in the high dimensional space based on the discriminative model; and determining an optimal matching of the at least one pose prediction in the high dimensional space to a current frame of the representation of human motion.

16. The computer program product of claim 15 wherein determining an optimal matching comprises steps of:

representing the current frame by a human body model comprising coordinates of joints and body parts having shapes associated with limbs, torso and head;

representing each pose prediction in the high dimensional space by the human body model; and selecting the pose prediction that optimally matches to the current frame based on the human body model.

17. The computer program product of claim 16 wherein the human body model comprises body part descriptors including one or more of a color histogram, a gradient orientation histogram, and a color distance histogram.

18. The computer program product of claim 14, wherein determining the P pose predictions comprises steps of:

determining a motion type of each of the nearest neighbors; and applying a dynamic model to each of the nearest neighbors based on the motion type, the dynamic model learned in a learning stage.

19. The computer program product of claim 14 wherein the discriminative model is received from a learning stage and wherein the learning stage is prior to said receiving steps, the learning stage comprising steps of:

receiving motion capture data from a motion capture source, the motion capture data comprising a first motion from a first motion class and a second motion from a second motion class that is different from the first motion class;

processing the motion capture data to extract a first sequence of pose states representing the first motion and a second sequence of pose states representing the second motion;

learning the discriminative model configured to project the first and second sequence of pose states to a low dimensional space and enforce discriminance between the first and second motion classes in the low dimensional space;

applying a clustering algorithm to the cluster temporally contiguous state vectors into the learned motion segments in the low dimensional space; and learning a dynamic model for each motion segment to generate motion predictions in the low dimensional space.

20. The computer program product of claim 19 wherein the clustering algorithm includes a k-means clustering algorithm.

21. The computer program product of claim 19 wherein learning the discriminative model includes applying a Local Discriminant Embedding (LDE) model.

22. The computer program product of claim 19 wherein learning a discriminative model comprises steps of:

computing an intra-class variety representing the sum of the distances between data points that are in the same motion class;

computing the inter-class separability representing the sum of the distances between data points that are in different motion classes;

obtaining a projection matrix configured to reduce the intra-class variety and increase the inter-class separability; and projecting the motion capture data from the high dimensional space to the low dimensional space based on the projection matrix.

23. The computer program product of claim 14 wherein the pose state comprises a vector of skeleton joint coordinates.

24. The computer program product of claim 14 wherein the at least one motion is tracked without background subtraction.

25. The computer program product of claim 14 wherein tracking the at least one motion comprises tracking the at least one motion in three dimensions.

* * * * *